United States Patent
Merdan et al.

(10) Patent No.: US 6,696,666 B2
(45) Date of Patent: Feb. 24, 2004

(54) TUBULAR CUTTING PROCESS AND SYSTEM

(75) Inventors: Kenneth M. Merdan, Greenfield, MN (US); Jan Weber, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 30 days.

(21) Appl. No.: 10/190,424

(22) Filed: Jul. 3, 2002

(65) Prior Publication Data

US 2004/0004061 A1 Jan. 8, 2004

(51) Int. Cl.$^7$ ............................................. B23K 26/38
(52) U.S. Cl. .................................................. 219/121.7
(58) Field of Search ........................ 219/121.7, 121.71, 219/121.72, 121.67, 121.68, 121.69, 121.63, 121.64, 121.65, 121.66; 29/557

(56) References Cited

U.S. PATENT DOCUMENTS 5,780,807 A * 7/1998 Saunders ............... 219/121.71
5,938,954 A * 8/1999 Onuma et al. .......... 219/121.84
6,211,485 B1 * 4/2001 Burgess .................... 219/121.7

FOREIGN PATENT DOCUMENTS

| EP | 0562150 B1 | 3/1992 |
| JP | 0562150 | 9/1993 |

* cited by examiner

Primary Examiner—Tom Dunn
Assistant Examiner—Jonathon Johnson
(74) Attorney, Agent, or Firm—Crompton, Seager & Tufte LLC

(57) ABSTRACT

A system and method for processing a tubular member comprises a hollow tubular member, a laser and a media flow. The laser is constructed and arranged to transmit laser energy to the tubular member. The laser energy is transmitted to the tubular member through a fluid column according to a predetermined pattern. The media flow is injected into the lumen of the hollow tubular member.

21 Claims, 1 Drawing Sheet

TUBULAR CUTTING PROCESS AND SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts, bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of bio-absorbable plastic materials. Stents have been formed from wire, tube stock, etc. Stents have also been made from sheets of material which are rolled.

A number of techniques have been suggested for the fabrication of stents from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter. Other references wherein laser cutting of stents is described include: U.S. Pat. No. 5,514,154, U.S. Pat. No. 5,759,192, U.S. Pat. No. 6,131,266 and U.S. Pat. No. 6,197,048.

A typical laser cutting system relies on a laser to produce a beam which is conditioned as necessary via an optical unit and focused into a spot beam which is impinged against a hollow tube that is to become the stent. The hollow tube may be moved via a rotational motor drive and linear motion drive.

An example of a conventional laser for cutting a stent is a highly focused pulsed Nd:YAG laser which has a pulse duration in the range of approximately 0.1 to 20 milliseconds. This is a long pulse time for cutting and characteristically produces a relatively large melt zone and heat affected zone (HAZ) on the metal. The conventional laser cutting process typically results in the formation of melt dross on the inside edge of the cut tube. This dross must be cleaned off in subsequent processes.

Non-uniformities in the material such as differences in wall thickness create different heat rises in the material and lead to variations in cut quality. Laser parameters have to be re-tuned for optimum cutting for tubes with slightly different wall thicknesses adding to the downtime of the process and reducing the yield. An additional drawback of cutting hollow tubes to produce stents by laser is that due to the extremely small diameter of the tubes, it is possible to damage the inner wall of the opposite side of the tube due to the inability of the laser to defocus to a level such that beam intensity is adequately low enough to prevent damage.

While laser energy has often been utilized for cutting stents, such laser energy has also been utilized for processing hypotubes and other substantially tubular bodies, such as may be used for producing catheters, balloons, etc. For example, in some cases laser energy may be utilized to create microfeatures in/on the surface of the tube being processed or to provide ports or other features through a tube wall. In processing hypotubes with laser energy, the potential for damage to the tube interior is also a problem.

In a recent development, cutting and processing systems have been developed that incorporate a water column and laser. SYNOVA Inc., of Lausanne, Switzerland, has developed a laser-microjet that uses a laser beam that is contained within a water jet as a parallel beam, similar in principle to an optical fiber.

The SYNOVA laser-microjet relies on low pressure water column to contain the laser, to reduce force applied to the work piece, to act as a cooling mechanism and to remove cutting debris. A laser-microjet as presently known however, may still include the potential to damage the inside surface of the hollow tube being cut or processed due to the inability of the laser to be properly defocused before damage can result.

In light of the above a need exists to provide a laser cutting/processing system wherein the potential for damage to the inside surface of the hollow tube being cut or processed is minimized or alleviated completely.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. In at least one embodiment the invention is directed to a system for cutting and/or processing a hollow tube. The system of the present embodiment utilizes a hybrid laser/water jet mechanism to direct laser energy to the tube. The system also employs an mechanism for injecting a media such as gas, fluid, etc, through the hollow tube in order to disrupt and/or prevent the formation of the water column within the tube. Such a disruption, results in deflection of the laser energy, thereby preventing the laser energy from reaching, and thus damaging, the opposite inside wall of the tube.

In at least one embodiment the hollow tube is a tube of a material suitable for constructing a stent, such a tube may be at least partially constructed from, stainless steel, nickel, titanium, palladium, gold, tantalum, or any other metal or alloy thereof suitable for constructing a stent. In at least one embodiment the tube is at least partially constructed from a polymer substance.

In at least one embodiment the hollow tube is a tube of material suitable for constructing a tubular medical device, or component thereof In the such an embodiment the processed tube may be utilized as, or a portion of: a hypotube, a catheter, a balloon, a sock, a sleeve, an embolic protection filter, etc.

In at least one embodiment the media being injected through the hollow tube is a fluid or gas. In some embodiments the media is injected through the tube at a pressure less than the pressure of the water jet being applied to the tube wall. In some embodiments it may be beneficial to provide the injected media with a degree of turbulence. In at least one embodiment turbulence may be induced by providing bubbles or micro-bubbles in the fluid media. In some embodiments the fluid media may include a dispersement of metallic or other absorptive and/or reflective particles to further disrupt the laser energy.

In at least one embodiment the media being passed through the tube is a high viscosity material or a material having a viscosity different than the viscosity of the water jet being applied to the tube wall.

In at least one embodiment the media that is passed through the tube functions as an oxidizer, cleaner, polishing agent, pretreatment, etc.

In at least one embodiment a secondary member is inserted into the tube during cutting or processing. The secondary member may be a rod, ribbon, a secondary hollow tube, etc. The secondary member and the tube may define an annulus through which media may continue to be passed.

In some embodiments the tube being processed is positioned in a vertical orientation during processing and/or cutting.

In some embodiments the tube being processed is positioned in a horizontal orientation during processing and/or cutting.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
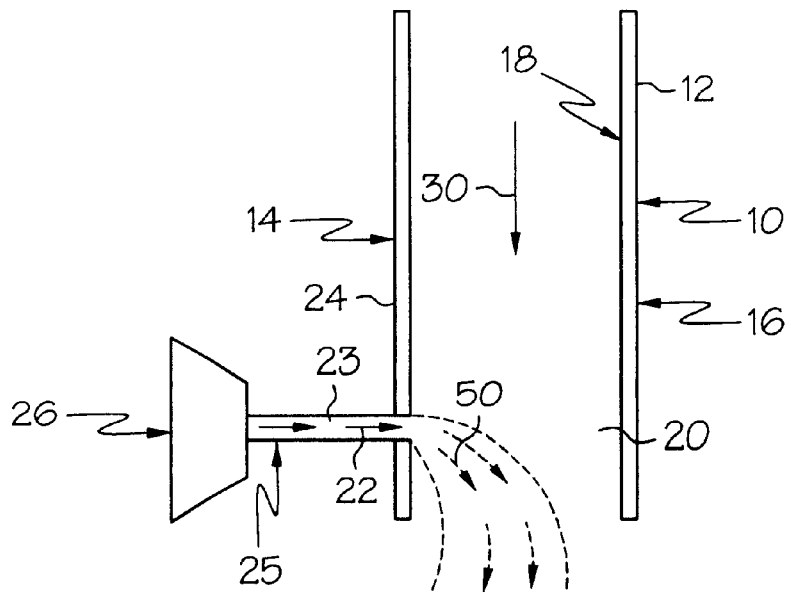
FIG. 1 is a cut-away side view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above the present invention is directed to a variety of embodiments. In at least one embodiment the invention is directed to a system for processing and/or cutting a hollow tubular body 10 such as is shown in FIG. 1.

In the embodiment shown, the hollow tubular body 10 may be any type of tube suitable for laser processing and/or cutting. Such a tube 10 may be a tubular member suitable for the construction of a stent, graft, stent-graft, vena cava filter, or other device suitable for implantation into a body lumen. Where the tube 10 is intended for the construction of a stent, the tube 10 will typically be at least partially constructed from a metal such as stainless steel, nickel, titanium, palladium, gold, tantalum, or any other metal or alloy thereof. In at least one embodiment tube 10 is constructed of a nickel-titanium alloy such as nitinol or other shape-memory alloys or materials.

Alternatively tube 10 may be a tubular member suitable for use in the manufacture of a catheter or portion(s) thereof. In such applications, the tube 10 will typically be constructed at least partially from one or more polymer substances including, but not limited to: polyester/polyether elastomers such as Arnitel™ available from DSM Engineering; polyurethane-polyether polymers, such as Tecothane™ and/or Tecoplast™ both being available from Thermedics, Inc.; polyester-polyurethanes, such as Pellethane™ sold by Dow Chemical; polyester-polyurethanes, such as Estane™ sold by BF Goodrich; polyether block amides (PEBA), such as Pebax™ available from Elf Atochem; styrene-butadien-styrene triblock copolymers, such as Kraton™ sold by Shell Chemical company; styrenic block copolymers; polyurethanes; silicone rubber; natural rubber; copolyesters; polyamides; EPDM rubber/polyolefin; nitril rubber/PVC; fluoroelastomers; butyl rubber; epichlorohydrin; block copolymers; polyethylene terephthalate (PET); polyethylene naphthalate (PEN); polybutylene terephthalate (PBT); poly-trimethylene terephthalate (PTT); poly lactic acid (PLA); fluoropolymers; polyolefins; polystyrene; polyvinyl chloride (PVC); acrylonitrile-butadiene-styrene polymers; polyacrylonitrile; polyacrylate; vinyl acetate polymer; cellulose plastics; polyacetal; polyethers; polycarbonates; polyphenylene sulfide; polyarylethersulfones; polyaryletherketones; polytetrafluoroethylene; polyamide copolymer, such as MXD6™ available from Mitsubishi Gas Chemical Co. or Cristamid™ available from Atofina; shape-memory polymers; liquid crystal polymers; bio-absorbable polymers; radiopaque polymers; MRI-visible polymers; etc.

Tube 10 may also include various coatings or surface materials, such as drug and/or drug vectors, lubricants, etc.

Regardless of the particular composition or the type of material used for tube 10, the tube comprises, includes a tube wall 12 having a first or processing side 14 and an opposing or second side 16, the interior surface 18 of the tube wall sides 14 and 16 define a passage or lumen 20.

In practice, at least a portion of one or more of the processing side 14 of the tube is initially is processed or cut by the application of laser energy, indicated by arrow 22. Preferably, laser energy 22 is transmitted through a column or stream of water or other solution referred to hereinafter as a fluid column 23. Fluid column 23 behaves similarly to a fiber optic in that the fluid column 23 allows the laser energy 22 to be focused and transmitted therethrough.

The combined stream of laser energy 22 and water column 23 is collectively referred to herein as a jet 25. The use of a hybrid laser/water jet for the purpose of cutting is known and commercially available laser/water jet mechanisms are commercially available from SYNOVA Inc., of Lausanne, Switzerland.

Where the tube 10 is to be processed into a stent, the tube 10 is rotated and/or repositioned to allow portions of the entire tube wall 12 to be eventually cut or otherwise processed. Similarly, where the tube is a hypotube the tube 10 may be positioned and/or moved to allow for one or more regions of the outside surface 24 of the tube 10 to be processed by jet 25. As indicated above, regardless of the type of tube 10, in some applications the laser energy 22 of the jet 25 may be applied to mark, cut, drill through or otherwise process one or more of the sides 14 and 16.

As is shown in FIG. 1 jet 25 is directed to the exterior 24 of the processing side 14 of the tube wall 12. Jet 25 is supplied by a laser-jet mechanism 26 such as is available from SYNOVA Inc. Mechanism 26 includes a laser which may be any type of laser suitable for use in processing tubular members. For example laser energy 22 may be energy supplied by a YAG laser, IR laser, UV laser, $CO_2$ laser, diode laser, etc. or any combination thereof.

In many tube processing applications, particularly stent cutting applications, laser energy 22 is applied eventually to both sides 14 and 16 of the tube 10 according to a predetermined cutting pattern. While both sides 14 and 16 may be processed and may even be cut through entirely by laser energy 22, it is often undesirable for the laser energy 22 to impact the interior surface 18 of the tube 10. Application of laser energy 22 to the interior surface 18 may result in damage to the tube interior inconsistent to the desired performance characteristics of the end product stent or hypotube.

To prevent such damage from occurring, the present invention utilizes a second fluid column or media flow, indicated by arrow 30, that is injected through the lumen 20 of the tube 10 during processing by jet 25. During processing if jet 25 penetrates the processing side 14 of the tube wall 12 media flow 30 may be injected into the lumen 20. In some embodiments media flow 30 is utilized to disrupt the fluid column 23 and thus laser energy 22 as the jet 25 passes into the lumen 20 (The disruption of the jet 25 and its components column 23 and energy 22 is illustrated by dashed line). As a result of the disruption caused by media flow 30, laser energy 22 is prevented from damaging the interior surface 18 of opposing side 16.

The media flow 30 may be composed of a variety of substances. For example media flow 30 may be primarily a fluid such as a gas or liquid with particulates of light absorbing and/or reflective particles of metal, graphite, etc. In some cases, media flow 30 may be a stream of liquid having bubbles and/or micro-bubbles therein. In yet another example, media flow 30 may be a solution of liquid having material dissolved therein, such that the resulting solution has some degree of energy reflecting and/or absorbing characteristics.

In addition to preventing laser energy 22 from damaging the tube interior 18, the media flow 30 provides the additional benefits of providing the tube with a natural cooling mechanism as well as aiding in drawing debris 50 away from the cutting site.

In some embodiments, the media flow 30 is comprised of a high viscosity fluid, solution or suspension. The viscosity of the media flow 30 and fluid column 23 may be varied to provide a variety of controlled flow effects. For example, during processing the media flow 30 changes the momentum of the fluid column 23 from radial to axial relative to the tube 10. This shift in momentum provides increased dimensional stability.

Figure 2:
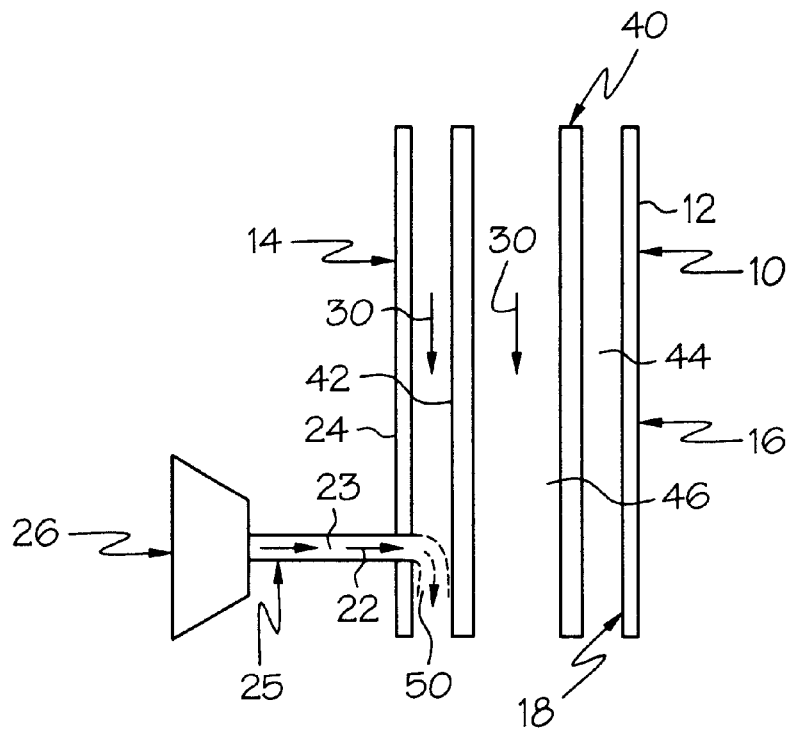
FIG. 2 is a cut-away side view of an embodiment of the invention wherein the hollow tube being processed includes a secondary member positioned therein.

In at least one embodiment, such as is shown in FIG. 2, lumen 20 may have a member 40 positioned therein. Member 40 may be a solid member, a second hollow tube, or any other elongated member. In at least one embodiment member 40 is a portion of the lathe or other device that retains and move tube 10 during processing. The member 40 may be substantially stationary or moveable relative to the tube 10.

In some embodiments, interior 18 of tube 10 and the exterior 42 of member 40 define an annular space, or annulus 44 through which media flow 30 is directed. In some embodiments, the member 40 acts as a secondary barrier in addition to media flow 30 for preventing laser energy 22 from damaging the second side 16. In some embodiments, the member 40 may be used exclusively.

In those embodiments where member 40 is hollow media flow 30 may also be passed through the lumen 46 defined by the member 40.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A system for processing a tubular member comprising:
   a hollow tubular member being defined by a tube wall, the tube wall defining a lumen;
   a laser, the laser constructed and arranged to transmit laser energy to the tubular member, the laser energy being transmitted to the tubular member through a fluid column according to a predetermined pattern;
   a media flow, the media flow being injected into the lumen of the hollow tubular member.

2. The system of claim 1 wherein the media flow is constructed and arranged to disrupt the fluid column and the laser energy transmitted therethrough.

3. The system of claim 1 wherein the media flow is constructed and arranged to remove dross from within the lumen.

4. The system of claim 1 wherein the hollow tubular member is metal.

5. The system of claim 1 wherein the hollow tubular member is a polymer.

6. The system of claim 1 wherein the fluid column comprises at least one liquid.

7. The system of claim 1 wherein the media flow comprises at least one liquid and at least one member of the group consisting of, gas, gas bubbles, gas micro-bubbles, particles of light reflective material, particles of light absorptive material, and any combination thereof.

8. The system of claim 1 wherein the media flow is an aerosol, a suspension or a solution.

9. The system of claim 1 wherein the laser is at least one member of the group consisting of: YAG laser, diode laser, IR laser, UV laser $CO_2$ laser and any combination thereof.

10. The system of claim 1 wherein the tube wall further comprises an inner surface and an outer surface, at least one of the inner surface and the outer surface having a coating.

11. The system of claim 1 further comprising an inner member, the inner member positioned within the lumen.

12. The system of claim 11 wherein the inner member is substantially stationary relative to the hollow tubular member.

13. The system of claim 11 wherein the inner member defines an exterior surface and the tube wall defines an inner surface, the inner surface of the tube wall and the exterior surface of the inner member defining an annular space, the media flow being injected into the annular space.

14. The system of claim 11 wherein the inner member is a second hollow tubular member having a second tube wall, the second tube wall defining an inner lumen, the media flow being injected into the inner lumen.

15. The system of claim 1 wherein the fluid column has a fluid viscosity and the media flow has a media viscosity.

16. The system of claim 15 wherein the fluid viscosity and the media viscosity are variable.

17. The system of claim 15 wherein the fluid viscosity and the media viscosity are different.

18. The system of claim 15 wherein the fluid viscosity and the media viscosity are the same.

19. The system of claim 1 wherein the fluid column has a predetermined application pressure and the media flow has a predetermined injection pressure, the predetermined injection pressure being less than the predetermined application pressure.

20. The system of claim 1 wherein the hollow tubular member is positioned in a vertically upright orientation relative to the laser.

21. The system of claim 1 wherein the hollow tubular member is positioned in a horizontal upright orientation relative to the laser.

* * * * *